United States Patent
Harding et al.

(10) Patent No.: US 10,265,514 B2
(45) Date of Patent: Apr. 23, 2019

(54) SENSING AND STIMULATION SYSTEM (71) Applicant: Medtronic, Inc., Minneapolis, MN (US)

(72) Inventors: William Harding, Chandler, AZ (US); Scott Mark, Roseville, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1057 days.

(21) Appl. No.: 14/181,074

(22) Filed: Feb. 14, 2014

(65) Prior Publication Data
US 2015/0231387 A1 Aug. 20, 2015

(51) Int. Cl.
*A61N 1/04* (2006.01)
*A61B 5/00* (2006.01)
*A61B 5/05* (2006.01)
*A61N 1/05* (2006.01)
*A61N 1/36* (2006.01)
*A61B 5/0408* (2006.01)
(Continued)

(52) U.S. Cl.
CPC .......... *A61N 1/0476* (2013.01); *A61B 5/0002* (2013.01); *A61B 5/0008* (2013.01); *A61B 5/0024* (2013.01); *A61B 5/05* (2013.01); *A61B 5/4836* (2013.01); *A61B 5/4851* (2013.01); *A61B 5/686* (2013.01); *A61N 1/0456* (2013.01); *A61N 1/05* (2013.01); *A61N 1/0551* (2013.01); *A61N 1/3605* (2013.01); *A61B 5/01* (2013.01); *A61B 5/04085* (2013.01); *A61B 5/1104* (2013.01); *A61B 5/224* (2013.01); *A61B 5/40* (2013.01); *A61B 5/42* (2013.01); *A61B 5/45* (2013.01); *A61B 5/4824* (2013.01); *A61B 5/6811* (2013.01); *A61B 5/6867* (2013.01); *A61B 5/6877* (2013.01); *A61B 2562/0247* (2013.01); *A61B 2562/0271* (2013.01); *A61B 2562/04* (2013.01); *A61B 2562/227* (2013.01); *A61N 1/0492* (2013.01); *A61N 1/36103* (2013.01)

(58) Field of Classification Search
CPC .......................... A61N 1/0476; A61B 2562/04
See application file for complete search history.

(56) References Cited

U.S. PATENT DOCUMENTS 5,544,661 A 8/1996 Davis et al.
6,049,730 A 4/2000 Kristbjarnarson
(Continued)

FOREIGN PATENT DOCUMENTS

CN 102271607 12/2011

OTHER PUBLICATIONS

PCT Search Report and Written Opinion for PCT/US2015/015352, dated May 6, 2015, 11 pgs.
(Continued)

*Primary Examiner* — Luther Behringer (57) ABSTRACT

A sensing and stimulation system includes a central hub, and a plurality of flexible arms extending from the central hub. Each of the arms includes at least one electrode and at least one sensor. Each of the arms is configured to perform sensing and stimulation including electrically stimulating biological material, and sensing biological responses and changes. The system includes a port configured to be alternatively connected to a remote control module for wireless operation of the system and a leaded connector for wired operation of the system.

15 Claims, 9 Drawing Sheets

(51) Int. Cl.
*A61B 5/01* (2006.01)
*A61B 5/11* (2006.01)
*A61B 5/22* (2006.01)

(56) References Cited

U.S. PATENT DOCUMENTS

| | | | |
|---|---|---|---|
| 6,402,689 B1 | 6/2002 | Scarantino et al. | |
| 6,768,921 B2 * | 7/2004 | Organ | A61B 5/0536 |
| | | | 600/300 |
| 7,035,692 B1 * | 4/2006 | Maghribi | A61N 1/0543 |
| | | | 600/383 |
| 7,215,991 B2 | 5/2007 | Besson et al. | |
| 7,272,428 B2 | 9/2007 | Hopman et al. | |
| 7,616,980 B2 | 11/2009 | Meyer | |
| 8,165,692 B2 * | 4/2012 | Strother | A61N 1/37276 |
| | | | 128/899 |
| 8,180,425 B2 * | 5/2012 | Selvitelli | A61B 5/04085 |
| | | | 600/382 |
| 2002/0072682 A1 | 6/2002 | Hopman et al. | |
| 2002/0099277 A1 | 7/2002 | Harry et al. | |
| 2004/0019369 A1 | 1/2004 | Duncan et al. | |
| 2005/0234525 A1 * | 10/2005 | Phillips | A61N 1/36021 |
| | | | 607/68 |
| 2005/0261559 A1 | 11/2005 | Mumford et al. | |
| 2006/0074460 A1 * | 4/2006 | Maghribi | A61N 1/0543 |
| | | | 607/53 |
| 2007/0027388 A1 | 2/2007 | Chou | |
| 2007/0123952 A1 | 5/2007 | Strother et al. | |
| 2007/0270672 A1 | 11/2007 | Hayter | |
| 2008/0177168 A1 * | 7/2008 | Callahan | A61B 5/04085 |
| | | | 600/382 |
| 2010/0130844 A1 * | 5/2010 | Williams | A61B 5/0478 |
| | | | 600/378 |
| 2010/0152811 A1 | 6/2010 | Flaherty | |
| 2011/0046506 A1 | 2/2011 | Durand et al. | |
| 2011/0082522 A1 * | 4/2011 | Bourget | A61N 1/37247 |
| | | | 607/59 |
| 2011/0152658 A1 * | 6/2011 | Peyser | A61B 5/01 |
| | | | 600/365 |
| 2011/0307274 A1 | 12/2011 | Thompson et al. | |
| 2011/0307284 A1 | 12/2011 | Thompson et al. | |
| 2012/0296191 A1 | 11/2012 | McGrath et al. | |
| 2012/0306662 A1 | 12/2012 | Vosch et al. | |
| 2013/0098678 A1 * | 4/2013 | Barker | A61N 1/3752 |
| | | | 174/563 |
| 2014/0031952 A1 * | 1/2014 | Harshbarger | A61F 2/72 |
| | | | 623/25 |
| 2014/0200496 A1 * | 7/2014 | Hyde | A61F 5/32 |
| | | | 602/19 |
| 2014/0288667 A1 * | 9/2014 | Oxley | A61N 1/3756 |
| | | | 623/25 |

OTHER PUBLICATIONS

Harding, "Sensing and Stimulation System", Chinese Patent Application No. 201580019479.6, First Chinese Office Action, Dispatched Nov. 20, 2018, 15 pps.

* cited by examiner

FIG. 12

SENSING AND STIMULATION SYSTEM

BACKGROUND

Conventional monitoring, diagnostic, and therapy equipment is typically structured in such a way that electrodes are mounted on the patient, which tap the respective signals and transmit such signals via cables to amplifier units. Such cables obstruct the patient and highly limit his or her freedom of movement. In addition, due to the stiffness of the cables and the forces connected therewith, the cables become easily detached particularly when the patient moves. Conventional therapy devices also typically provide stimulation to a broad area in a "shotgun" approach, rather than just providing stimulation to the specific areas in need.

SUMMARY

One embodiment is directed to a sensing and stimulation system. The system includes a central hub, and a plurality of flexible arms extending from the central hub. Each of the arms includes at least one electrode and at least one sensor. Each of the arms is configured to perform sensing and stimulation including electrically stimulating biological material, and sensing biological responses and changes. The system includes a port configured to be alternatively connected to a remote control module for wireless operation of the system and a leaded connector for wired operation of the system.

Another embodiment is directed to a sensing and stimulation system. The system includes a central hub, and a plurality of flexible arms extending from the central hub. Each of the arms includes at least one electrode and at least one sensor. Each of the arms is configured to perform sensing and stimulation including electrically stimulating biological material, and sensing biological responses and changes. The system includes a remote control module configured to control the sensing and stimulation, transmit and receive wireless signals, and receive sensor data from a prosthetic device and control the stimulation based on the received sensor data.

Yet another embodiment is directed to a method of providing sensing and stimulation for a body. The method includes providing a system including a central hub and a plurality of flexible arms extending from the central hub, wherein each of the arms includes at least one electrode and at least one sensor. The method includes adjusting a length of at least one of the arms, and attaching each of the arms, including the at least one arm with an adjusted length, to the body. The method includes performing sensing and stimulation with the attached arms, including electrically stimulating biological material, and sensing biological responses and changes.

DETAILED DESCRIPTION

Figure 1:
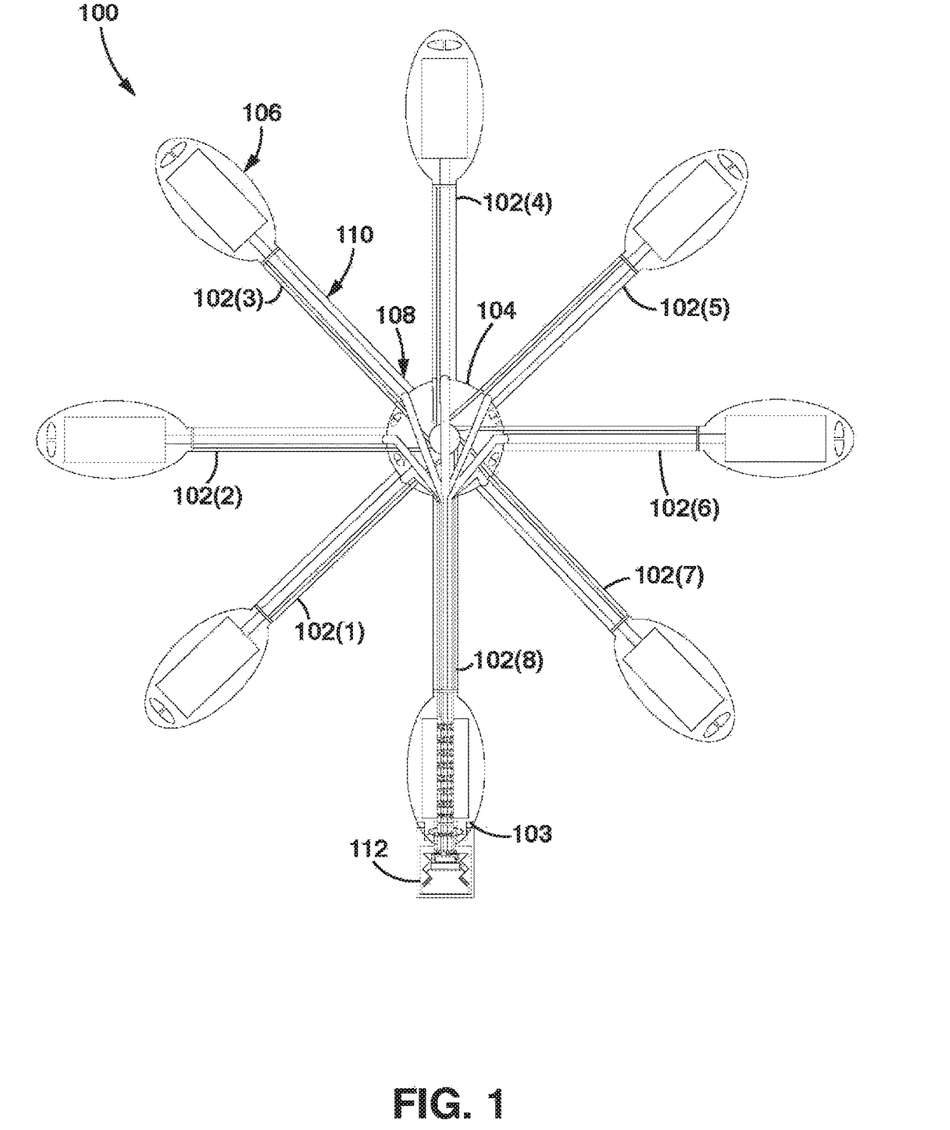
FIG. 1 is a diagram illustrating a top view of a sensing and stimulation system according to one embodiment.

FIG. 1 is a diagram illustrating a top view of a sensing and stimulation system 100 according to one embodiment. Sensing and stimulation system 100 includes eight flexible arms 102(1)-102(8) (collectively referred to as arms 102) extending radially outward from a central hub 104. The arms 102 include a primary arm 102(8) and seven secondary arms 102(1)-102(7). Each arm 102 includes a distal end portion 106, a proximal end portion 108, and a central portion 110 that extends between the end portions 106 and 108. The proximal end portion 108 of each arm 102 is connected to the central hub 104. In one embodiment, system 100 has an overall diameter of about 5 mm or less.

System 100 may be used in either a wireless (or leadless) configuration or a wired (or leaded) configuration. In the embodiment shown in FIG. 1, the system 100 is in a wireless configuration, and includes a remote control module 112 plugged into a port 103 in the distal end 106 of the primary arm 102(8). The remote control module 112 is described in further detail below with reference to FIGS. 9 and 10. In the wired configuration, the remote control module 112 is not used, and the system 100 is directly connected to another device via a leaded connector 300 (FIG. 3), which is plugged into port 103.

Figure 2:
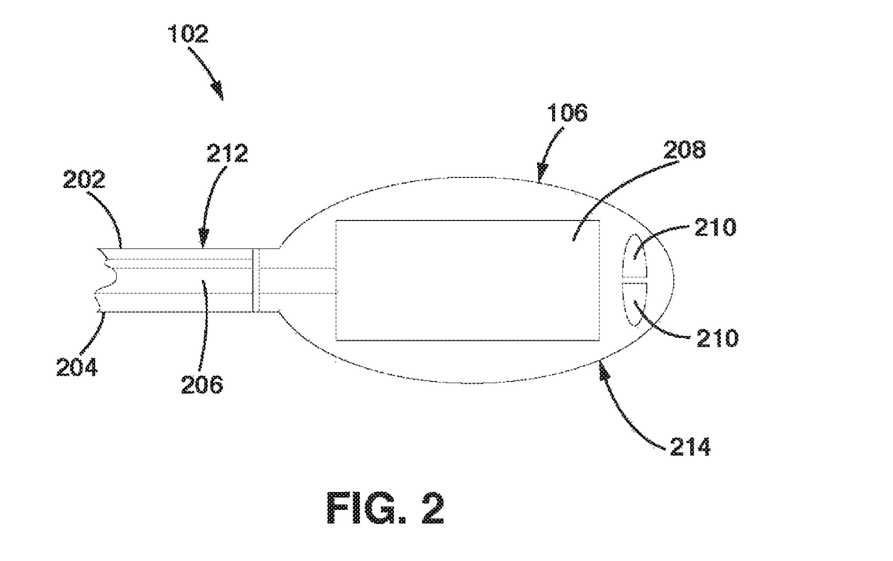
FIG. 2 is a diagram illustrating a close-up view of the distal end portion of one of the arms of the system shown in FIG. 1 according to one embodiment.

FIG. 2 is a diagram illustrating a close-up view of the distal end portion 106 of one of the arms 102 of the system 100 shown in FIG. 1 according to one embodiment. In one embodiment, the arms 102 of system 100 are all configured in substantially the same manner shown in FIG. 2. As shown in FIG. 2, the distal end portion 106 includes an arm portion 212 and an oval-shaped electrode portion 214. The arm portion 212 has a smaller width than the electrode portion 214, and extends to the central hub 104. The electrode portion 214 extends distally from the arm portion 212, and has a larger width than the arm portion 212. The electrode portion 214 includes a conductor plate 208 and stitch points 210. The conductor plate 208 has a rectangular shape in the illustrated embodiment, and is connected to a lead wire 206. The stitch points 210 are positioned distal to the conductor plate 208, and facilitate attachment (e.g., via stitching) of the arm 102 to a patient.

The arm portion 212 includes thermal sensor wire (e.g., thermally active material) 202, insulator (e.g., a biocompatible polymer) 204, and lead wire 206. Thermal sensor wire 202 extends laterally across the arm portion 212 adjacent to the electrode portion 214, and then extends longitudinally along the arm 102 to the central hub 104. Lead wire 206 is attached to conductor plate 208 and extends longitudinally along the arm 102 to the central hub 104. Insulator 204 encloses and electrically insulates thermal sensor wire 202 and lead wire 206 along the length of the arm 102. In one embodiment, wire 202 also acts as a pressure sensor. In another embodiment, a separate pressure sensing element is positioned along the length of the arm 102.

Figure 3:
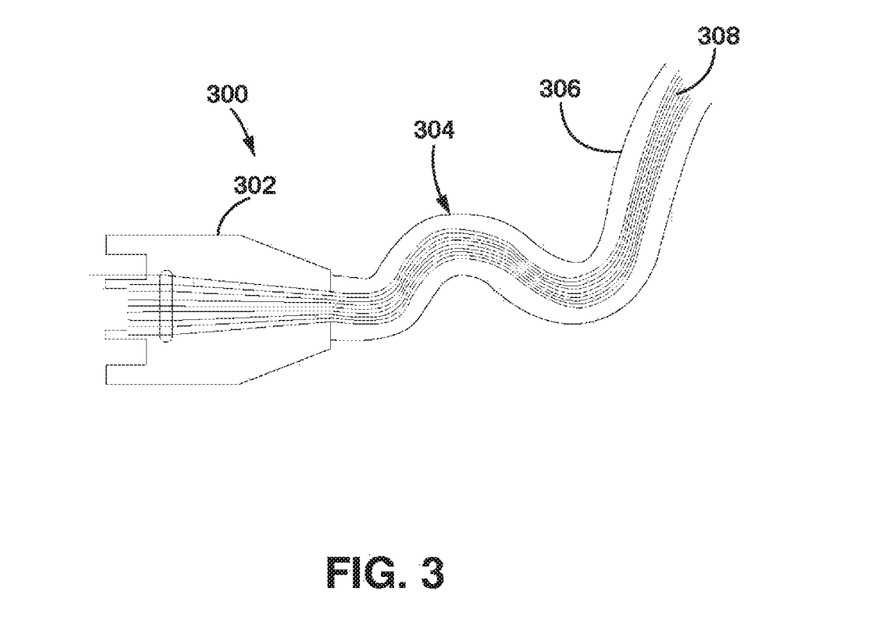
FIG. 3 is a diagram illustrating a close-up view of a leaded connector of the system shown in FIG. 1 according to one embodiment.

FIG. 3 is a diagram illustrating a close-up view of a leaded connector 300 of the system 100 shown in FIG. 1 according to one embodiment. As mentioned above, in the wired configuration, the remote control module 112 is not used, and the system 100 is directly connected to another device via leaded connector 300. Leaded connector 300 includes connector 302 and flexible lead 304. Connector 302 is configured to be plugged into the port 103 at the distal end of the primary arm 102(8). Flexible lead 304 includes wires 308 and insulator 306, and is configured to be attached to another device. Insulator 306 surrounds and electrically insulates the wires 308 along the length of the flexible lead 304. The wires 308 extend through the connector 302, and are configured to be electrically coupled to electrical connections of the system 100.

Figure 4:
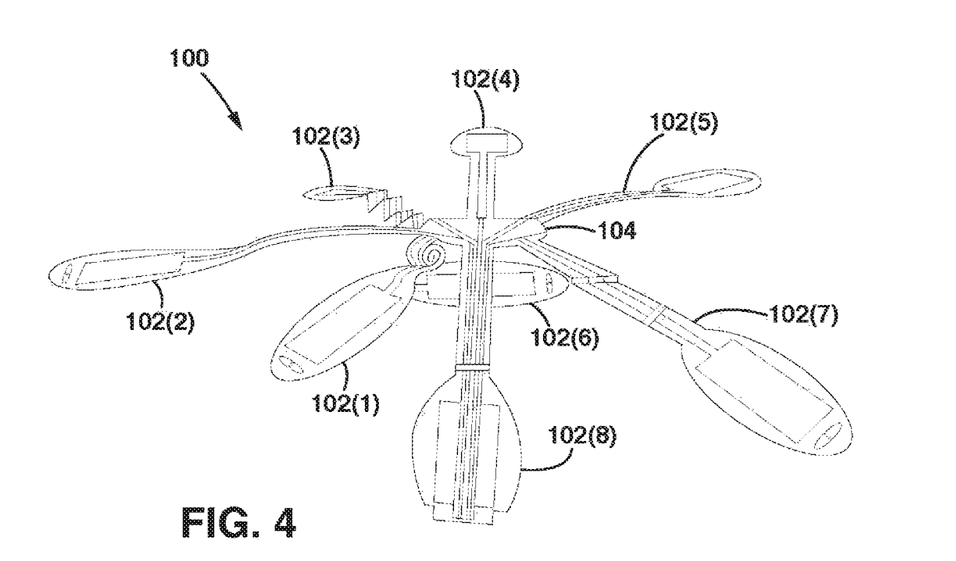
FIG. 4 is a diagram illustrating a perspective view of the system shown in FIG. 1, with arms of the system rolled up or folded up according to one embodiment.

FIG. 4 is a diagram illustrating a perspective view of the system 100 shown in FIG. 1, with arms of the system 100 rolled up or folded up according to one embodiment. As shown in FIG. 4, the arm portion 212 of arm 102(1) has been rolled up, which effectively shortens the length of arm 102(1) and causes the electrode portion 214 of arm 102(1) to be positioned closer to the central hub 104. The arm portion 212 of arm 102(3) has been folded up in an accordion-like manner, which shortens the length of arm 102(3) and causes the electrode portion 214 of arm 102(3) to be positioned closer to the central hub 104. Arm 102(6) has been folded such that the electrode portion 214 is positioned directly under the central hub 104. Arms 102(1), 102(3), and 102(6) may be extended out to any desired length (up to a fully extended state) during deployment. The length of each arm 102 is adjustable, and manipulating the arms 102 of the system 100 as shown in FIG. 4 facilitates an easier and more accurate deployment of the system 100.

Figure 5:
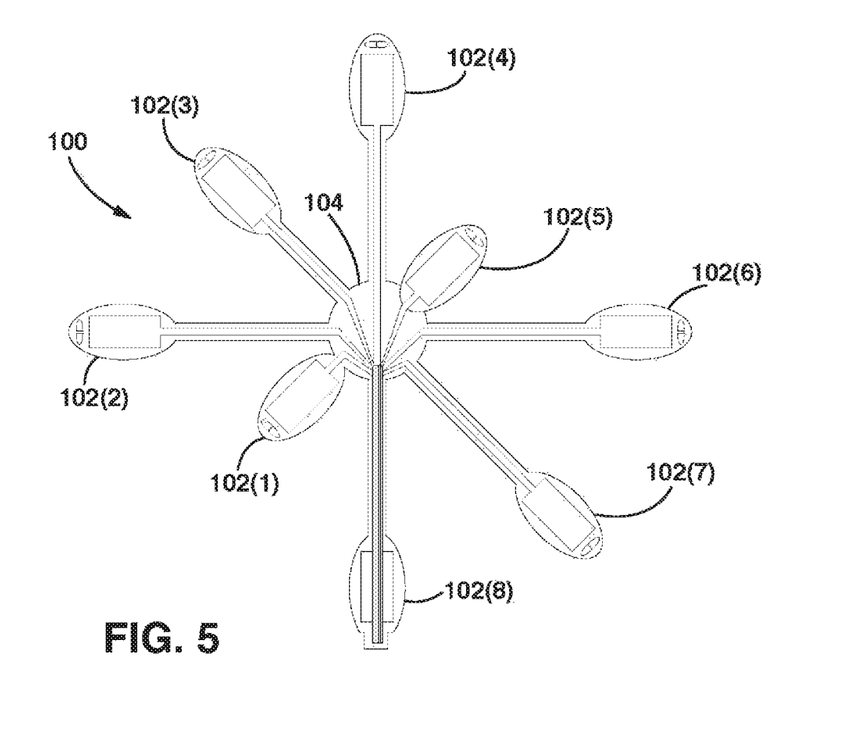
FIG. 5 is a diagram illustrating a top view of the system shown in FIG. 1, with arms of the system rolled up or folded up according to one embodiment.

FIG. 5 is a diagram illustrating a top view of the system 100 shown in FIG. 1, with arms of the system 100 rolled up or folded up according to one embodiment. As shown in FIG. 5, the arm portions 212 of arms 102(1) and 102(5) have been completely rolled up or folded up, which effectively shortens the lengths of these arms and causes the electrode portions 214 of these arms 102 to be positioned directly adjacent to the central hub 104. The arm portion 212 of arm 102(3) has been partially rolled up or folded up, which effectively shortens the length of this arm and causes the electrode portion 214 of this arm 102(3) to be positioned closer to the central hub 104 than the electrode portions 214 of arms 102(2), 102(4), 102(6), 102(7), and 102(8), which are completely extended. Manipulating the arms 102 of the system 100 as shown in FIG. 5 facilitates an easier and more accurate deployment of the system 100.

Figure 6:
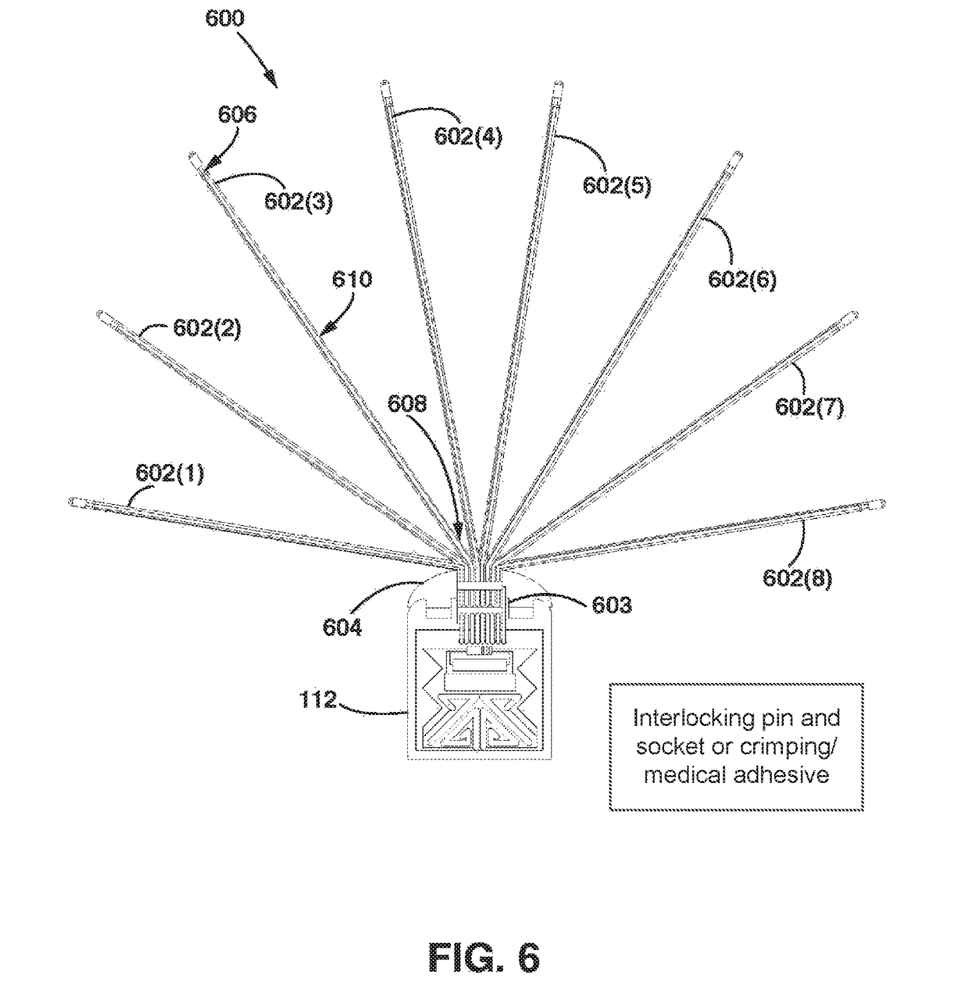
FIG. 6 is a diagram illustrating a top view of a sensing and stimulation system according to another embodiment.

FIG. 6 is a diagram illustrating a top view of a sensing and stimulation system 600 according to another embodiment. Sensing and stimulation system 600 includes eight flexible arms 602(1)-602(8) (collectively referred to as arms 602) extending radially outward from a central hub 604. Each arm 602 includes a distal end portion 606, a proximal end portion 608, and a central portion 610 that extends between the end portions 606 and 608. The proximal end portions 608 of the arms 602 are connected together at the central hub 604. In one embodiment, system 600 has an overall diameter of about 5 mm or less.

System 100 (FIG. 1) according to one embodiment has a star configuration in which the arms 102 extend radially outward from the central hub 104 at eight evenly spaced positions 360 degrees around the central hub 104. In contrast, system 600 (FIG. 6) according to one embodiment has a half-star configuration in which the arms 602 extend radially outward from the central hub 604 at eight evenly spaced positions 180 degrees around the central hub 604.

System 600 may be used in either a wireless (or leadless) configuration or a wired (or leaded) configuration. In the embodiment shown in FIG. 6, the system 600 is in a wireless configuration, and includes a remote control module 112 plugged into a port 603 at the central hub 604. The remote control module 112 is described in further detail below with reference to FIGS. 9 and 10. In the wired configuration, the remote control module 112 is not used, and the system 600 is directly connected to another device via a leaded connector 800 (FIG. 8), which is plugged into port 603.

Figure 7:
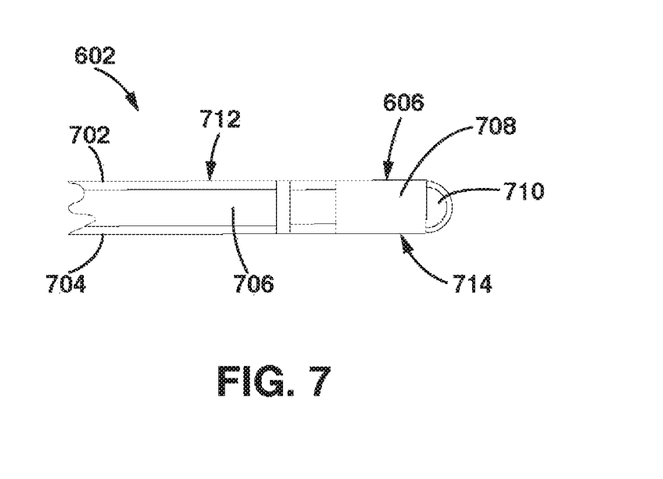
FIG. 7 is a diagram illustrating a close-up view of the distal end portion of one of the arms of the system shown in FIG. 6 according to one embodiment.

FIG. 7 is a diagram illustrating a close-up view of the distal end portion 606 of one of the arms 602 of the system 600 shown in FIG. 6 according to one embodiment. In one embodiment, the arms 602 of system 600 are all configured in substantially the same manner shown in FIG. 7. As shown in FIG. 7, the distal end portion 606 includes an arm portion 712 and an electrode portion 714. The arm portion 712 has the same width as the electrode portion 714, and extends to the central hub 604. The electrode portion 714 extends distally from the arm portion 712. The electrode portion 714 includes a conductor 708 and stitch point 710. The conductor 708 is connected to a lead wire 706. The stitch point 710 is positioned distal to the conductor 708, and facilitates attachment (e.g., via stitching) of the arm 602 to a patient.

The arm portion 712 includes thermal sensor wire (e.g., thermally active material) 702, insulator (e.g., a biocompatible polymer) 704, and lead wire 706. Thermal sensor wire 702 extends laterally across the arm portion 712 adjacent to the electrode portion 714, and then extends longitudinally along the arm 602 to the central hub 604. Lead wire 706 is attached to conductor 708 and extends longitudinally along the arm 602 to the central hub 604. Insulator 704 encloses and electrically insulates thermal sensor wire 702 and lead wire 706 along the length of the arm 602. In one embodiment, wire 702 also acts as a pressure sensor. In another embodiment, a separate pressure sensing element is positioned along the length of the arm 602.

Figure 8:
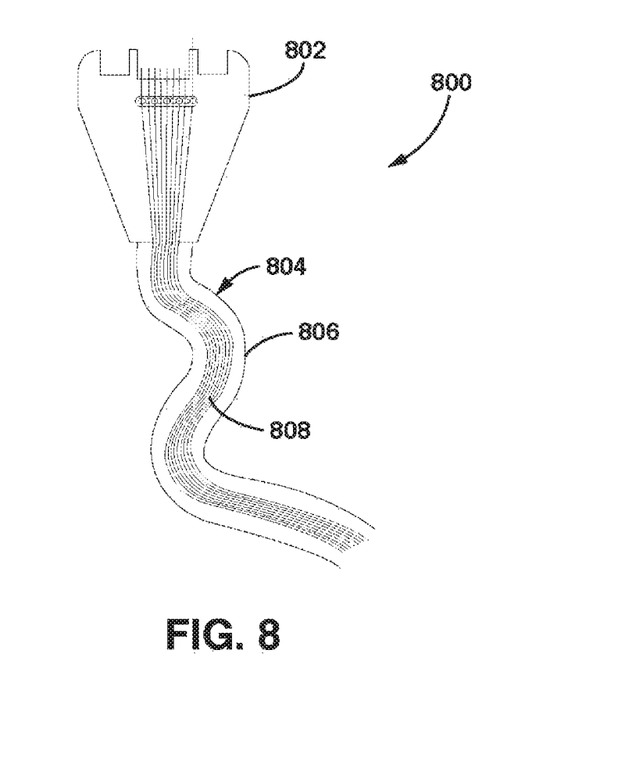
FIG. 8 is a diagram illustrating a close-up view of a leaded connector of the system shown in FIG. 6 according to one embodiment.

FIG. 8 is a diagram illustrating a close-up view of a leaded connector 800 of the system 600 shown in FIG. 6 according to one embodiment. As mentioned above, in the wired configuration, the remote control module 112 is not used, and the system 600 is directly connected to another device via leaded connector 800. Leaded connector 800 includes connector 802 and flexible lead 804. Connector 802 is configured to be plugged into the port 603 at the hub 604. Flexible lead 804 includes wires 808 and insulator 806, and is configured to be attached to another device. Insulator 806 surrounds and electrically insulates the wires 808 along the length of the flexible lead 804. The wires 808 extend through the connector 802, and are configured to be electrically coupled to electrical connections of the system 600.

Figure 9:
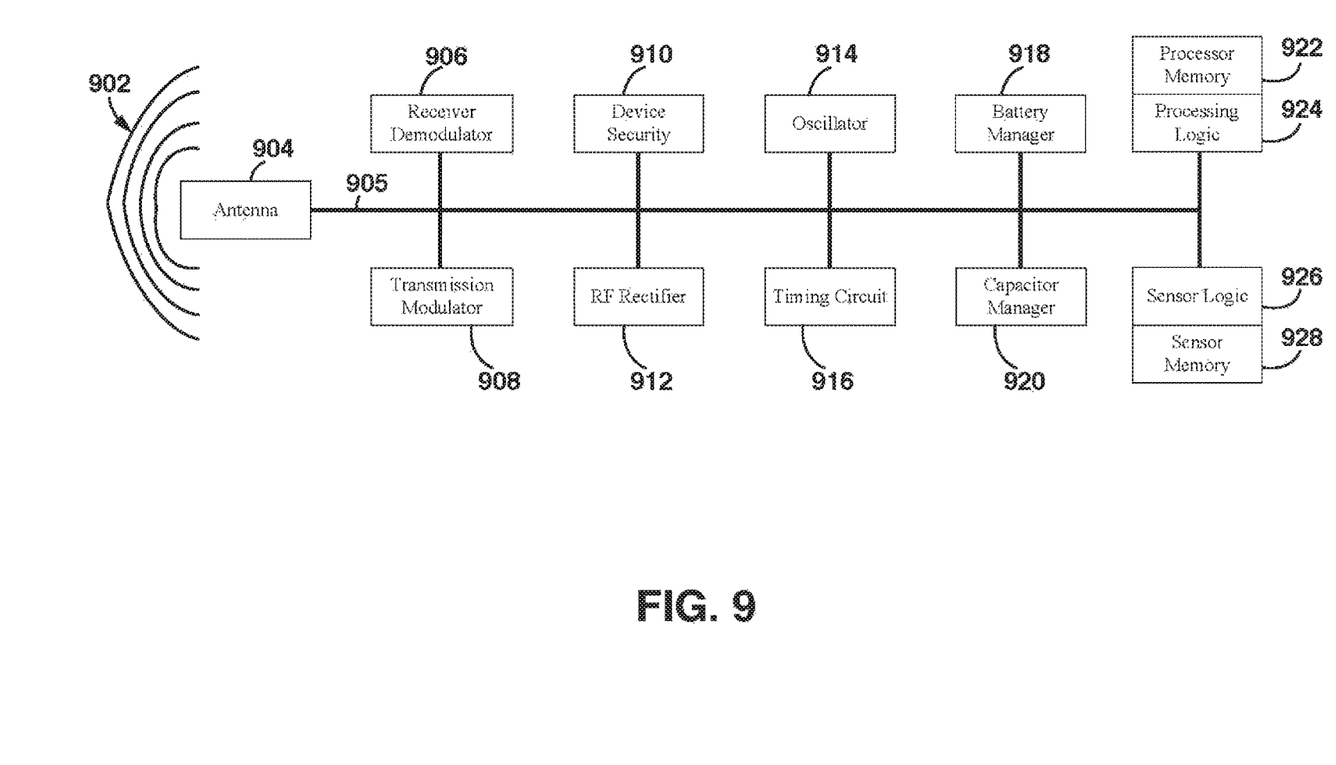
FIG. 9 is a block diagram illustrating components of the remote control module shown in FIGS. 1 and 6 according to one embodiment.

FIG. 9 is a block diagram illustrating components of the remote control module 112 shown in FIGS. 1 and 6 according to one embodiment. Remote control module 112 includes antenna 904, receiver demodulator 906, transmission modulator 908, device security module 910, radio frequency (RF) rectifier 912, oscillator 914, timing circuit 916, battery manager 918, capacitor manager 920, processor memory 922, processing logic (processor) 924, sensor logic 926, and sensor memory 928. These elements are communicatively coupled together via communications and power bus 905.

Antenna 904 is used by module 112 to send and receive RF energy (e.g., RF signals) 902. Receiver demodulator 906 demodulates received RF signals and detects commands. Receiver demodulator 906 also extracts the clock from the received RF signals, which is used to synchronize the RF transponder with the RF transceiver. Transmission modulator 908 modulates received data (e.g., transponder ID and sensor data) for transmission to an RF transceiver. Device security module 910 ensures transponder to transceiver filtering (dense reader mode), restricts/controls transponder access, and regulates signal/ambient RF energy. RF rectifier 912 rectifies the input RF signal and manages/generates a DC voltage to power the other blocks of the module 112. In one embodiment, the total power consumption of module 112 is 1 µW or less.

Oscillator 914 according to one embodiment is a switching/intermittent oscillator module that is used to convert an internal voltage into a pulsed signal. Timing circuit 916 comprises an internal clock that supplies an internally generated timing signal to digital elements of the RF transponder, which control the use of multiple timers as would be used to establish therapy delivery/stimulation and sensing rates. Additionally, the timing circuit 916 enables dynamic configuration of stimulation/sensing rates, hibernation states, data collection frequency sample rates, and transmission wake-up/duration. Battery manager 918 provides primary circuit power, current regulation, battery temperature monitoring, and power status. Module 112 includes a rechargeable battery 1006 (FIG. 10) that stores excess rectified RF energy such as transceiver and ambient energy. Battery manager 918 is used to extend battery life of battery 1006. Capacitor manager 920 regulates an adjustable capacitor 1004 (FIG. 10) and works in conjunction with the oscillator module 914 to control pulse modulation, width/duration, frequency, and intensity.

Processor memory 922 stores data for processing logic 924. Processing logic 924 is a digital part (e.g., microcontroller) of the module 112, and controls all other blocks of the module 112. Additionally, processing logic 924 stores the transponder ID, processes device instructions, determines when to collect data and when to transmit data, and when to hibernate. Sensor logic 926 controls electrical and thermal sensing, including sensor sample timing, results collection, and storage of sensor results data in sensory memory 928.

To limit possible interference with other electrical devices, the RF transponder according to one embodiment communicates via inductive coupling using the high frequency (HF) of 13.56 MHz. The RF transponder frequency of 13.56 MHz complies with standards classified worldwide as ISM (industrial, scientific, medical) frequency ranges for use in ISM environments or by short range devices (SRD) frequency.

Figure 10:
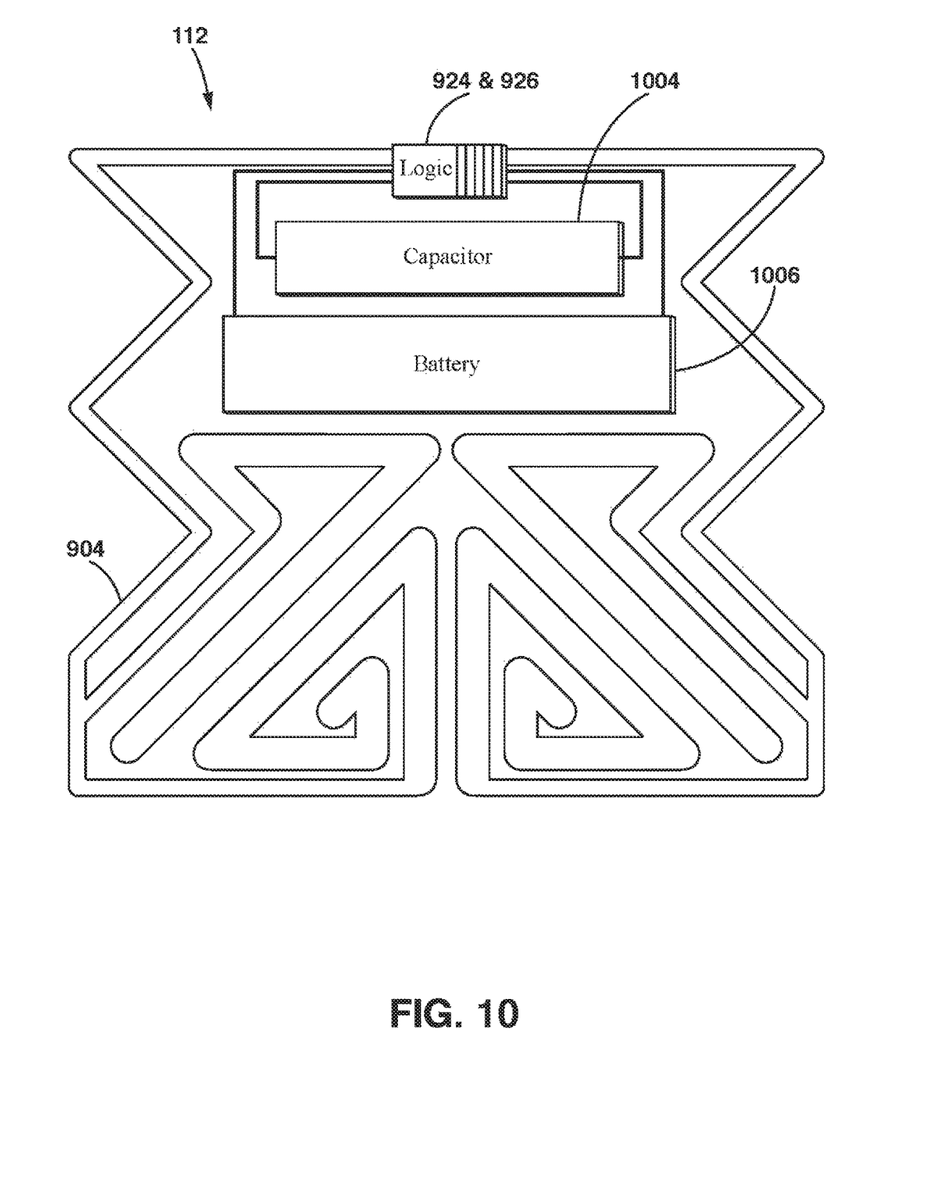
FIG. 10 is a diagram illustrating a remote control module according to one embodiment.
Figure 11:
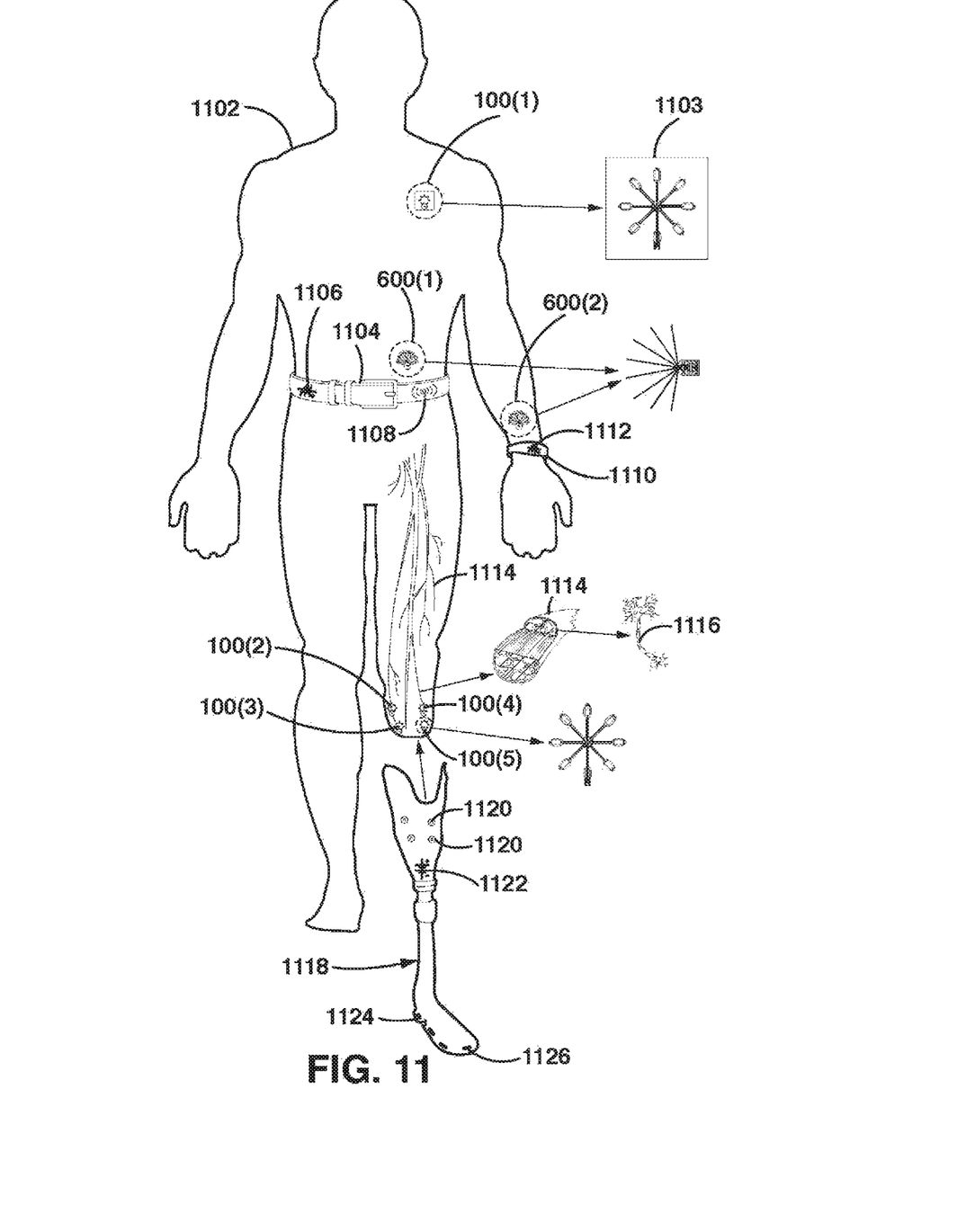
FIG. 11 is a diagram illustrating example uses of the sensing and stimulation systems according to one embodiment.

FIG. 10 is a diagram illustrating a remote control module 112 according to one embodiment. In addition to the elements shown in FIG. 9, including logic elements 922 and 926 and antenna 904, module 112 also includes capacitor 1004 and battery 1006. In one embodiment, capacitor 1004 is a 1 µW (or less) capacitor, and battery 1006 is a 200 uAhr rechargeable battery. Antenna 904 according to one embodiment is a compressed, fractal antenna FIG. 11 is a diagram illustrating example uses of the sensing and stimulation systems 100 and 600 according to one embodiment. As shown in FIG. 11, multiple systems 100 and 600 have been applied to a patient 1102. Specifically, system 100(1), which is in a wireless configuration with an included remote control module 112, has been applied to the chest of the patient via an epidermis patch 1103. System 600(1), which is in a wireless configuration with an included remote control module 112, has been applied at a subdermal level at the patient's abdomen. System 600(2), which is in a wireless configuration with an included remote control module 112, has been applied at a subdermal level at the patient's forearm. Systems 100(3), 100(4), 100(5), and 100(6), which are each in a wireless configuration with an included remote control module 112, are implanted on nerve bundles 1114 below the patient's knee. As shown in FIG. 11, the nerve bundles 1114 include neurons 1116.

The patient 1102 is wearing a belt 1104, which includes a rechargeable power source 1106, and an RF transceiver 1108 that is configured to communicate with systems 100 and 600. The patient 1102 is also wearing a wrist band 1110, which includes an RF transceiver 1112 that is configured to communicate with systems 100 and 600.

Prosthesis 1118 is configured to be attached to the leg of the patient 1102. Prosthesis 1118 includes a rechargeable power source 1122, and RF transceivers 1120 that are configured to communicate with systems 100 and 600. Prosthesis 1118 also includes pressure sensors 1124 and proximity sensors 1126. Sensors 1124 and 1126 generate sensor data that is transmitted to systems 100(2), 100(3), 100(4), and 100(5) via transceivers 1120. Systems 100(2), 100(3), 100(4), and 100(5) use this received sensor data to generate appropriate stimulation signals.

The systems 100 and 600 shown in FIG. 11 may be used to provide the user with direct and/or remote sensing responses, such as pressure, pain (neurological), cardiopulmonary, temperature, gastroenterology, skeletal, etc. Usage of systems 100 and 600 may include the collection and transfer of non-biological stimulation to the user/target such as provided from a gaming console, robot, prosthetic, wristband, patch, or other non-biological entities. Nodal relationships between remote controlled systems 100 and 600 are via a secure protocol with a unique identification for each system 100 or 600.

Figure 12:
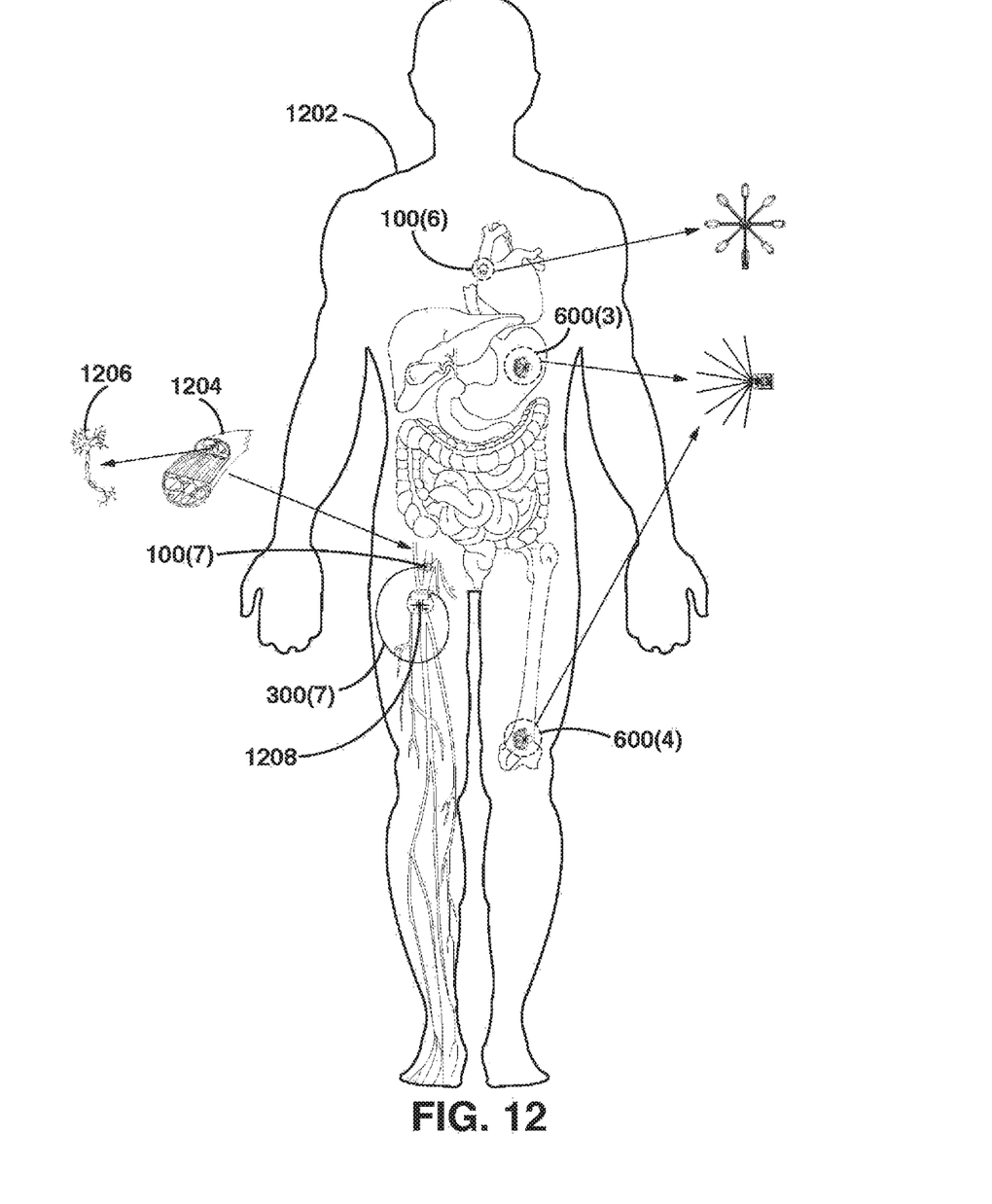
FIG. 12 is a diagram illustrating example uses of the sensing and stimulation systems according to another embodiment.

FIG. 12 is a diagram illustrating example uses of the sensing and stimulation systems 100 and 600 according to another embodiment. As shown in FIG. 12, multiple systems 100 and 600 have been applied to a patient 1202. Specifically, system 100(6), which is in a wireless configuration with an included remote control module 112, has been implanted and applied to the patient's heart. System 600(3), which is in a wireless configuration with an included remote control module 112, has been implanted and applied to the patient's stomach. System 600(4), which is in a wireless configuration with an included remote control module 112, has been implanted and applied to the patient's femur. System 100(7), which is in a wired configuration with an included leaded connector 300(7), has been implanted on nerve bundles 1204 on the patient's leg. As shown in FIG. 12, the nerve bundles 1204 include neurons 1206. The connector 300(7) is connected to device 1208, which is a stimulation device in one embodiment. Device 1208 according to one embodiment is configured to communicate with system 100(7) via the leaded connector 300(7), and is configured to wireless communicate with systems 100(6), 600(3), and 600(4).

The systems 100 and 600 shown in FIG. 12 may be used to provide the user with direct and/or remote stimulation and sensing responses, such as pressure, pain (neurological), cardiopulmonary, temperature, gastroenterology, skeletal, etc. Nodal relationships between remote controlled systems 100 and 600 and direct connect systems 100 and 600 is via a secure protocol with a unique identification for each system 100 or 600.

System 100 (FIG. 1) and system 600 (FIG. 6) according to one embodiment are multi-armed implantable (or externally attached) devices configured to electrically stimulate biological material, and sense biological responses and changes (e.g., nerves, tissue, muscles, skeletal, and fluids), within the body's electrical system, including changes in the temperature of surrounding tissue and pressure changes associated with movement or increased tension. The systems 100 and 600 can be configured to perform substantially similar functions, and are also referred to herein as system 100/600. The system 100/600 according to one embodiment is referred to as a spider sensing and stimulation system (S4) specifically because of its use of multiple arms such as may be visually similar to a spider.

At the end of each arm 102/602 in the electrode portion 214/714, electrical signals are sent to, or received from, biological regions based on programmable requirements/parameters (e.g., electrical sensing/stimulation of pulse modulate, width/duration, frequency, and intensity), while along the length or axis of each arm 102/602, the system 100/600 detects and transmits any thermal variations of surrounding tissue as well as pressure changes. Though the number of arms 102/602, length of the arms 102/602, and size of system 100/600 may vary based on need, the system 100/600 according to one embodiment creates stimulation/sensing from each arm 102/602, between two opposing arms 102/602, between multiple implementations of the system 100/600 (e.g., connected in a nodal configuration), and/or between implementations of system 100/600 and sensor/stimulator devices (e.g., implanted using leads or external using telemetry [e.g., wireless communications]).

The system 100/600 according to one embodiment provides patients and medical professionals with programmable stimulation therapy and sensing (e.g., pain sensing, pulse modulation, width/duration, frequency, intensity, and temperature and pressure sensing) through the use of a compact multi-purpose device 100/600 that is able to be deployed both as an implant and external to the patient. Data collection is through interrogation, analysis, and system 100/600 has the ability to "learn" based on sensing history.

The biocompatible configurable system 100/600 is able to function as a single stimulation point (specific polarity) or in changing patterns, which rotate in various directions, intensity, and polarity, or in a nodal relationships between remote controlled implementations of system 100/600 (which includes mixed configurations [e.g., leaded configurations and leadless or remote control module configurations]).

Additionally, the system 100/600 is configured to store specific secure patient baseline data, such as base core body temperature (for different times of the day and events), normal pain thresholds, glucose alert thresholds/normal range, acceptable pressure variants, normal cardiac rhythms, gastro responses, limit values, and health specific data used to determine if an abnormal event has occurred, as well as when and how to react to a specific event (e.g., alert/notification, automatic response therapy [e.g., such as pain control]).

System 100/600 may be used for Neuro, Cardiac, Gastro, Ortho, Diabetes, etc. System 100/600 can be utilized for a variety of methods, including the following: (1) Method for sensing and controlling pain and neurological responses at a point of need; (2) method for providing muscular stimulation (such as with newly grafted muscles); (3) method for transmitting electrical signals between two points where there are barriers to electrical transmission (e.g., from amputation, nerve damage) or where a connection is needed between an external device (such as a prosthetic) and the patient's internal electrical system; (4) method for determining current temperature, abnormal temperature variations of surrounding tissue, and core body temperature; (5) method for sensing cardiac rhythms/signals and stimulating cardiac fluids and tissue; (6) method for sensing gastro signals and stimulating gastro organs, fluids, and tissue; (7) method for sensing orthopedic signals and stimulating bones in addition to associated components (e.g., bone morphogenetic protein [BMP]); (8) method of providing the user (signal receiver) with remote sensing responses (such as pressure, pain, temperature, etc.); (9) method for determining non-cardiac/non-neurological electrical signals within any biological environment; (10) method for detecting neuroglycopenia (severe neurological hypoglycemia) associated with diabetes and impaired brain function; and (11) method for detecting pressure changes in muscular structures (extension/contraction) and skeletal structures (growth/fusing) as well as changes in gastro organs as a means to determine movement and associated indicators of health.

Note that usage of system 100/600 may include the collection and transfer of non-biological stimulation to/from the user/target such as provided from a gaming console, robot, prosthetic, or other non-biological entities. In one embodiment, system 100/600 comprises a modified transcutaneous electrical nerve stimulation (TENS) unit to provide stimulation between two attachments points of opposing polarity.

In one embodiment, system 100/600 senses and relays variances detected in the neurological system (e.g., impedance, reaction frequency, and spikes [from normal baseline]), using a suitable conductive material (e.g., within biocompatible polymer(s)). Sensing by system 100/600 may also be used during surgeries (e.g., Spinal, Cardiac, Neuro, Ortho, Diabetes, etc.) as a method for determining patient response (for example, when a medical instrument moves from/through one area to another of divergent density/resistance [e.g., tissue, bone, muscle] alerting the physician of the transition). Additionally, system 100/600 is able to relay a patient's subtle biological reactions/responses (e.g., pain guarding response(s)) where the patient may be sedated and unable to respond appropriately. With the ability to detect neurological changes (within both the central nervous system [CNS] and the peripheral nervous system [PNS] [sensory nerves and motor nerves (somatic/autonomic nerves)]), the system 100/600 also possesses the ability to provide an automatic response to those changes (+/−) such as adjusting pain therapy that might be normally made available via an implanted neurostimulator. A system 100/600 deployed to provide peripheral nerve field stimulation (PNFS) is very similar to direct spinal cord stimulation (CNS), but instead involves placing the arms of the system 100/600 just under the skin (subdermal) in an area near to the target nerves (such as those involved in pain).

Use of system 100/600 is not limited to neurological, cardiopulmonary, orthopedic, gastroenterology, obesity, or diabetes usage models and may be also used to sense any thermal variations, pressure changes, and electrical signals that are produced within a biological environment (such as within the anatomy of a human or nonhuman patient), where the system 100/600 may be placed internal (e.g., epidermis level) and external. By including the ability to sense temperature changes (e.g., using thermally reactive material) in the patient, the system 100/600 may be used for early detection and notification of an infection, circulatory concern, and other health related issues. Additionally, the system 100/600 may be used to monitor changes in core body temperature, which can be an indicator of numerous health states. With the average normal body temperature being that of 98.2° Fahrenheit and a temperature over 100.4° Fahrenheit generally being an indicator of infection or illness, monitoring those changes in a patient's temperature with system 100/600 will assist with applying appropriate therapy/treatment by system 100/600. It should also be noted that since a patient's fever threshold baseline varies during the day, a proper calibration of the system 100/600 is provided to account for a patient's specific temperature variations such that the best results will be used in alerting of an abnormal event/condition. Additionally, with the ability of system 100/600 to detect pressure changes (relative to each arm 102/602), the system 100/600 is able to determine movement associated variations within the target patient's muscular and skeletal structure (from baseline parameters).

Additionally, the system 100/600 can serve as a system to detect severe episodes of hypoglycemia through neurological sensing of neuroglycopenia (a potentially fatal event when low glucose reduces brain function such that a patient is no longer able to respond). The system 100/600 can also be used independently or as a backup to other glucose monitoring/control systems in the prevention of severe hypoglycemia, as well as integrated with insulin delivery therapies as part of a "closed loop" diabetes monitoring and control system. When deployed on the surface of the stomach or other gastrointestinal areas, the pressure/motion detection features of the system 100/600 can be used in the monitoring and treatment of obesity (e.g., through gastric expansion sensing and feedback, detection and recordation of the onset of food intake or detection of certain gastric related sounds) or other gastric disorders such as gastroparesis.

Placement of the system 100/600 may vary from placement as a patch on the patient's epidermis, within a wearable bracelet/ring/clothing/patch, subcutaneous insertion (subdermal) such as performed during an out-patient procedure, to placement deep within the patient's body (percutaneous or disambiguation) as performed during surgical procedures where the patient is placed under general anesthesia. Placement of the system 100/600 may be through known implant methods such as used in the practice of neurological, cardiopulmonary, orthopedic, diabetes, or gastroenterology lead placement. Additional methods for deployment may be procedurally such that an arm 102/602 of system 100/600 is inserted, stimulation pad attached, insertion tool retracted, next arm 102/602 is inserted, attached, tool retracted (and so on) until all arms 102/602 of the system 100/600 have been deployed. Once all arms 102/602 of the system 100/600 are deployed, then the remote control module 112 (in a wireless configuration) or the leaded connector 300/800 may be joined with the wires of the arms 102/602, such that the remote control module 112 or leaded connector 300/800 cuts excess wire, electrically isolates each lead and arm wire, seals the module 112 or connector 300/800 to the arm wires, locks the system using both interlocking pin and socket or crimping/medical adhesive, and then creates an electrical link to the remote control module 112 circuitry or primary stimulation device I/O.

In one embodiment, each arm 102/602 of system 100/600 can be connected to the target area without the need to use methods that may themselves cause additional patient issues. Stitch points 210/710 or micro hooks can be used on the end of each arm 102/602, or a more passive method of adhesion or anchoring can be used.

An implanted system 100/600 is able to provide direct therapy to targeted areas of the patient. The system 100/600 allows for multiple methods of control and transmission of electrical signals (e.g., wired, wireless [e.g., radio frequency (RF)], and/or both). The wired method of control of system 100/600 according to one embodiment is via a leaded connector 300/800 attached to an implanted medical device capable of controlling multiple implementations of system 100/600. The wireless remote control method of control of system 100/600 is via an individually attached rechargeable/inductively charged remote control module 112. The attached remote control module 112 contains encapsulated circuitry that can be programmed remotely, perform preprogrammed functions, and be recharged inductively (using for example RF energy).

Embodiments of system 100/600 with the wireless control module 112 work independent or in a nodal relationship. In one embodiment, the nodal relationships between remote controlled systems 100/600 (or mixed configurations of systems 100/600 [leaded and leadless]) are via a secure protocol with unique identification for each system 100/600.

System 100/600 may be adhered to a patient/user using stitches, micro hooks, or anchors to secure arm contact points, or a medical adhesive as a less intrusive method, without complicating or adding to potential/existing health issues. System 100/600 can be deployed as a purely inductively powered device (passive), inductively charged device (semi-passive), and as an internally powered rechargeable device (active) that combine the use of batteries and capacitors. In one embodiment, system 100/600 is a multi-mode device that is configured to automatically switch between a passive mode, a semi-passive mode, and an active mode.

Four methods for deploying system 100/600 and electrically connecting the remote control module 112 or leaded connector 300/800 will now be described. The first deployment method involves the following steps: (1) Insert the system 100/600 with arms 102/602 retracted (see, e.g., FIGS. 4 and 5 and corresponding description) until the system 100/600 reaches the center point of the target; (2) extend deployment tool to a target location; (3) connect a single arm 102/602 to target location; (4) retract deployment tool to center point; (5) for each arm 102/602, repeat the process of extending to a target location, attaching arm 102/602 to target location, and retracting the deployment tool to the center point; (6) connect the remote control module 112 or the leaded connector 300/800 by pushing the module 112 or connector 300/800 into the system 100/600, and locking the module 112 or connector 300/800 in position using a crimping method combined with the use of a medical adhesive; and (7) activate the system 100/600 using an external user/physician wireless control module and/or an implanted stimulation/sensing device.

The second deployment method involves the following steps: (1) Use a catheter insertion tool to insert an arm 102/602 to the target location (where therapy will be delivered); (2) attach the arm 102/602; (3) retract the catheter insertion tool, leaving the arm 102/602 in place; (3) for each arm 102/602, repeat the insert, attach, and retract steps until all of the arms 102/602 are in place; (5) join either the remote control module 112 or leaded connector 300/800 to the system 100/600 such that the joining includes cutting the excessive arm wire; electrically connecting the module 112 or connector 300/800 to the arm wires; sealing the connection point physically (such as might be used with a pin and socket); and sealing the connection point with medical adhesive; and (6) activate the system 100/600 using an external user/physician wireless control module and/or an implanted stimulation/sensing device.

The third deployment method involves the following steps: (1) embed the system 100/600 with a connected remote control module 112 within an adhesive patch/bandage and apply over a target sensing/stimulation site (e.g., heart, nerve group, feet, wrist, shoulder, etc.); and (2) activate the system 100/600 with an external user/physician wireless control module.

The fourth deployment method involves the following steps: (1) deploy the system 100/600 with a connected remote control module 112 as described by either the first or second deployment methods described above; (2) activate the system 100/600 with an external user/physician wireless control module; and (3) provide continuous charge, communications, data storage, and updated programming through a wearable rechargeable transceiver device such as a wristband, belt, anklet or device interwoven into the patient clothing. External collection/control devices are configured with enough internal memory and power to allow for usage outside of any interfacing "Target Area".

Usage models for system 100/600 include, but are not limited to, employing multiple systems 100/600 in multiple configurations in a wireless mesh network, where network nodes and associated devices are integrated into the environment of the defined space (see "Target Areas" below) and where the wireless mesh network is able to provide continuous telemetry (may include inductive charging)/control/communications with the system(s) 100/600.

Users of system 100/600 may have the ability to collect health related data such that the data can be used to provide improved health monitoring, response, and notification to patients/clients and secure health systems. Collected data may be (as configured by the user) transmitted to medical professionals/systems (e.g., clinic, ER, hospital, primary care physician, dentist, pharmacist, wellness system, etc.). Data collected by the system 100/600 will be used to assist with "learning" and optimizing the internal sensing algorithms, response/therapy, and notifications and behaviors of system 100/600. In addition to system 100/600 providing real-time sensing and stimulation, collected data from system 100/600 can be used by predictive (statistical) systems such as would help provide a pre-diagnosis of a negative medical/health condition. With respect to notification systems, a user of system 100/600 might be informed of serious health risks (e.g., cardiopulmonary, neurological, gastroenterology, orthopedic, respiratory, diabetes, cancer, etc.) and also be notified of less critical issues associated with diet, dehydration, temperature, or potential signs of, for example, a common cold.

The following is a description of some target areas for use of system 100/600. A first target area is a home. A home environment would most likely combine all elements found within all other target areas, with the addition of data that might be collected from the home air conditioning system (e.g., air quality, humidity, temperature), bath, shower, sink, toilet, security system (e.g., motion detectors measuring user activity), refrigerator/freezer/pantry/cabinets (tracking food/dietary intake, medicine), TV/gaming system (IR/motion sensing), audio system, water softener, etc. User notification could be through home entertainment systems, device displays (as shown for example on a fridge display panel). Example areas within this target area include, for example, the following: kitchen, bedroom, living room, dining room, family room, garden, home office, and bathroom.

A second target area is medical facilities/physical therapy clinics/primary care physician offices/dentist offices/pharmacy. Medical facilities deploying systems that are able to interface with system 100/600, may incorporate all means of collecting (interfacing) and controlling data as discussed herein. With the potential added benefit of patient tracking, users of system 100/600 may interface with systems such as those shown in U.S. Published Patent Applications Nos. 2011-0307284 and 2011-0307274, which are hereby incorporated by reference herein. This can help optimize work flow management, ensuring the timely application of medical therapy and the coordination of medical resources. Example areas in this target area include, for example, the following: waiting room, admitting area, diagnosis areas (e.g., X-Ray, MRI, Ultrasound, etc.), recovery room, surgical room, examination room, bathrooms, patient (overnight) rooms, and prescription pickup.

A third target area is work. Office environments can be used to monitor normal health indicators as well as data that might indicate elevated stress, the need to take a break/stretch, take prescribed medicine, drink water, etc. Though it may not be feasible to configure/calibrate a work environment's entire wireless mesh network to suit each individual, much of the same data collected within a home environment would also be desired in a work environment. Example areas in this target area include, for example, the following: desk environment, conference room(s), workout area, parking lot, and cafeteria/break room.

A fourth target area is school. For pediatric applications in particular, the school environment has similarities to the home and work environments along with some elements of a primary care environment in the form of a student health office and a paraprofessional health practitioner who assists with care. Many of the same environmental factors could participate in the sensing system, along with predictable schedules (such as physical education, recess, and other high activity events) and known nutrition information from school lunch programs to optimize sensing and therapy. Alerts could go to students, teachers, teaching assistants, the student health office, and other individuals participating in a patient's secondary care. Example areas in this target area include, for example, the following: gymnasium, cafeteria, health office, and classroom.

A fifth target area is gym/sports complex. Facility equipment/systems linked to fitness routines/workout programs, class schedules, etc. are additional examples of environments for use with embodiments disclosed herein. Users of system 100/600 may track normal biological responses such as calories burned, cardiac rhythms, respiratory response (along with any abnormal conditions) while assisting the user with achieving improved health (e.g., muscle and bone strength, oxygen absorption, improved metabolism). Example areas in this target area include, for example, the following: Fitness room, pool, spinning room, yoga area, and spa.

A sixth target area is car/bus/van pool. A road vehicle environment may also collect data from the vehicle air conditioning system, audio system, as well as an internalized wireless mesh network. User notification could be through the vehicle entertainment system and the primary in-dash display.

A seventh target area is airport/airplane/jet. In addition to data collected from system 100/600 via the internalized wireless mesh network, the monitoring of a flying vehicle's air quality, temperature, cabin pressure, etc. could be very valuable in determining patient risks (such as dehydration, thickening of the blood, circulatory issues, viral risks, etc.).

An eighth target area is a grocery store. An interactive environment would use an individual's unique data (such as an online grocery list) combined with in-store data as provided during the process of shopping or at checkout. User notification (related to user needs, interactions with other items, healthy choices, etc.) could be through a mobile phone (or other mobile device) and/or via a grocery cart with an integrated user interface. Data collected from the grocery store (specific to the individual) would be transmitted to the user's personal data repository where it would be used in conjunction with all other user collected data to assist the user in maintaining a healthy life style/environment.

There should be no assumed limitations of where system 100/600 could be used or any environment where monitoring/control/notification systems could be deployed (e.g., restaurants, grocery stores, libraries, schools, etc.). Though this disclosure mentions wireless mesh networks, the tools that could be used to interface to system 100/600 could be as simple as a mobile phone (remote access point), laptop, TV, etc.

To supplement the environment and to improve a user's interaction with interfaced in-home systems as well as with system 100/600, a reader/scanner/antenna (1D, 2D, RFID) may be employed, which is able to identify and track items placed and pulled to/from a storage location. Another solution would be one device with an interface where the user could input data and select storage locations. Information stored in the home system could also be gathered from a grocery store system (see target areas above) and combined to form a more complete health/wellness picture. That information may relate to dietary information (contents), servings, expiration, storage requirements (cold, dry, warm, etc.), usage (paper towels, toiletries, cleaning supplies, etc.), safety (proximity to other items, not to be frozen, keep out of reach of children, too many consumed [e.g., aspirin or cold medicine], etc.), pharmacy items (might also link to a person's schedule for taking required medicine, or when a prescription might expire, drug reactions or how a particular drug should be taken [with food/liquid, before bed time, etc.], etc.). The home system would also be adaptive to provide for interfacing with items created in the home (e.g., liquids, meals, home grown, canned, etc.) where those items would be individually tagged (using a reusable tag [e.g., RFID]) such that the home systems could track those items (e.g., usage, expiration, user entered details, etc.).

One embodiment is directed to a sensing and stimulation system. The system includes a central hub, and a plurality of flexible arms extending from the central hub. Each of the arms includes at least one electrode and at least one sensor. Each of the arms is configured to perform sensing and stimulation including electrically stimulating biological material, and sensing biological responses and changes. The system includes a port configured to be alternatively connected to a remote control module for wireless operation of the system and a leaded connector for wired operation of the system.

In one embodiment, the system is configured to receive sensor data from a prosthetic device and generate stimulation signals based on the received sensor data. The remote control module according to one embodiment is configured to control the sensing and stimulation and transmit and receive RF signals. In one embodiment, an overall length of each of the arms is individually adjustable. The at least one sensor included in each arm is configured to detect thermal variations along substantially an entire length of the arm. In one embodiment, the at least one sensor is configured to detect pressure changes.

In one embodiment, the plurality of flexible arms includes at least eight flexible arms extending radially outward from a central hub, and wherein a proximal end of each of the arms is connected to the central hub. In one form of this embodiment, a distal end of one of the arms includes the port. In another embodiment, the central hub includes the port. In one embodiment, the at least eight flexible arms are arranged in a star configuration in which the arms extend radially outward from the central hub at evenly spaced positions 360 degrees around the central hub. In another embodiment, the at least eight flexible arms are arranged in a half-star configuration in which the arms extend radially outward from the central hub at evenly spaced positions 180 degrees around the central hub.

The system according to one embodiment is configured to automatically switch between a passive mode, a semi-passive mode, and an active mode, wherein the system is purely inductively powered in the passive mode, inductively charged in the semi-passive mode, and internally powered with a rechargeable battery in the active mode. In one embodiment, the system is configured to store health specific data used to determine if an abnormal event has occurred, and is configured to automatically react to the abnormal event with response therapy.

Another embodiment is directed to a sensing and stimulation system. The system includes a central hub, and a plurality of flexible arms extending from the central hub. Each of the arms includes at least one electrode and at least one sensor. Each of the arms is configured to perform sensing and stimulation including electrically stimulating biological material, and sensing biological responses and changes. The system includes a remote control module configured to control the sensing and stimulation, transmit and receive wireless signals, and receive sensor data from a prosthetic device and control the stimulation based on the received sensor data.

In one embodiment, an overall length of each of the arms is individually adjustable. The at least one sensor included in each arm according to one embodiment is configured to detect thermal variations along substantially an entire length of the arm.

In one embodiment, the plurality of flexible arms includes at least eight flexible arms extending radially outward from a central hub, and wherein a proximal end of each of the arms is connected to the central hub. In one form of this embodiment, the at least eight flexible arms are arranged in a star configuration in which the arms extend radially outward from the central hub at evenly spaced positions 360 degrees around the central hub. In another embodiment, the at least eight flexible arms are arranged in a half-star configuration in which the arms extend radially outward from the central hub at evenly spaced positions 180 degrees around the central hub.

Yet another embodiment is directed to a method of providing sensing and stimulation for a body. The method includes providing a system including a central hub and a plurality of flexible arms extending from the central hub, wherein each of the arms includes at least one electrode and at least one sensor. The method includes adjusting a length of at least one of the arms, and attaching each of the arms, including the at least one arm with an adjusted length, to the body. The method includes performing sensing and stimulation with the attached arms, including electrically stimulating biological material, and sensing biological responses and changes.

Although the present disclosure has been described with reference to preferred embodiments, workers skilled in the art will recognize that changes can be made in form and detail without departing from the spirit and scope of the present disclosure.

What is claimed is:

1. A sensing and stimulation system, comprising:
   a central hub;
   a plurality of flexible anus extending from the central hub, wherein each of the arms includes at least one electrode and at least one sensor, and wherein each of the arms is configured to perform sensing of biological responses and changes, and electrically stimulating biological material using electrical signals;
   a remote control module configured to generate the electrical signals with voltage and current levels sufficient to provide pain therapy when delivered to the biological material using at least one of the arms; and
   a port configured to be alternatively connected to the remote control module for wireless operation of the system and a leaded connector for wired operation of the system.

2. The system of claim 1, wherein the system is configured to receive sensor data from a prosthetic device and generate the stimulation signals based on the received sensor data.

3. The system of claim 1, wherein the remote control module is connected to the port and configured to transmit and receive wireless radio frequency (RF) signals.

4. The system of claim 1, wherein an overall length of each of the arms is individually adjustable.

5. The system of claim 4, wherein a central portion of each of the arms is configured to individual adjust a corresponding length of the arm by rolling up of the arm.

6. The system of claim 1, wherein the system is configured to identify variations in muscular structure in response to the temperature sensor detecting thermal variations along substantially an entire length of the arms.

7. The system of claim 1, wherein the system is configured to detect movement by comparing sensed pressure from a pressure sensor to baseline parameters.

8. The system of claim 1, wherein the plurality of flexible arms includes at least eight flexible arms extending radially outward from the central hub, and wherein a proximal end of each of the arms is connected to the central hub.

9. The system of claim 8, wherein a distal end of one of the arms includes the port.

10. The system of claim 8, wherein the central hub includes the port.

11. The system of claim 8, wherein the at least eight flexible arms are arranged in a star configuration in which the arms extend radially outward from the central hub at evenly spaced positions 360 degrees around the central hub.

12. The system of claim 8, wherein the at least eight flexible arms are arranged in a half-star configuration in which the arms extend radially outward from the central hub at evenly spaced positions 180 degrees around the central hub.

13. The system of claim 1, wherein the system is configured to automatically switch between a passive mode, a semi-passive mode, and an active mode, wherein the system is purely inductively powered in the passive mode, inductively charged in the semi-passive mode, and internally powered with a rechargeable battery in the active mode.

14. The system of claim 1, wherein the system is configured to store health specific data used to determine if an abnormal event has occurred, and is configured to automatically react to the abnormal event with response therapy.

15. The system of claim 1, wherein the pain therapy is a stimulation therapy selected from the group consisting of transcutaneous electrical nerve stimulation and peripheral nerve field stimulation.

* * * * *

UNITED STATES PATENT AND TRADEMARK OFFICE
CERTIFICATE OF CORRECTION

PATENT NO. : 10,265,514 B2
APPLICATION NO. : 14/181074
DATED : April 23, 2019
INVENTOR(S) : William Harding and Scott Mark It is certified that error appears in the above-identified patent and that said Letters Patent is hereby corrected as shown below:

In the Claims

Column 15, Line 16 (Claim 1): Replace "flexible anus" with -- flexible arms --
Column 15, Line 40 (Claim 5): Replace "individual adjust" with -- individually adjust --
Column 16, Line 3 (Claim 6): Replace "the temperature sensor" with -- a temperature sensor --

Signed and Sealed this
Twentieth Day of August, 2019

Andrei Iancu
*Director of the United States Patent and Trademark Office*